(12) United States Patent
Nam et al.

(10) Patent No.: US 11,986,551 B2
(45) Date of Patent: *May 21, 2024

(54) SEDATIVE LACED TOOTHPASTE

(71) Applicants: Daniel S. Nam, Oakland, CA (US); Eugene Kwon, Oakland, CA (US)

(72) Inventors: Daniel S. Nam, Oakland, CA (US); Eugene Kwon, Oakland, CA (US)

( * ) Notice: Subject to any disclaimer, the term of this patent is extended or adjusted under 35 U.S.C. 154(b) by 273 days.

This patent is subject to a terminal disclaimer.

(21) Appl. No.: 17/326,067

(22) Filed: May 20, 2021

(65) Prior Publication Data

US 2021/0275436 A1     Sep. 9, 2021

Related U.S. Application Data

(63) Continuation of application No. 16/728,256, filed on Dec. 27, 2019, now Pat. No. 11,026,881.

(60) Provisional application No. 62/787,708, filed on Jan. 2, 2019.

(51) Int. Cl.

| | | |
|---|---|---|
| *A61K 8/86* | (2006.01) |
| *A61K 8/25* | (2006.01) |
| *A61K 8/34* | (2006.01) |
| *A61K 8/365* | (2006.01) |
| *A61K 8/368* | (2006.01) |
| *A61K 8/49* | (2006.01) |
| *A61K 8/73* | (2006.01) |
| *A61K 8/92* | (2006.01) |
| *A61K 8/96* | (2006.01) |
| *A61K 8/9789* | (2017.01) |
| *A61Q 11/00* | (2006.01) |

(52) U.S. Cl.
CPC .............. *A61K 8/9789* (2017.08); *A61K 8/25* (2013.01); *A61K 8/345* (2013.01); *A61K 8/347* (2013.01); *A61K 8/365* (2013.01); *A61K 8/368* (2013.01); *A61K 8/498* (2013.01); *A61K 8/731* (2013.01); *A61K 8/733* (2013.01); *A61K 8/737* (2013.01); *A61K 8/86* (2013.01); *A61K 8/92* (2013.01); *A61K 8/965* (2013.01); *A61Q 11/00* (2013.01)

(58) Field of Classification Search
None
See application file for complete search history.

(56) References Cited

U.S. PATENT DOCUMENTS

| | | | |
|---|---|---|---|
| 11,026,881 B2 * | 6/2021 | Nam ..................... A61K 8/73 |
| 2016/0166498 A1 * | 6/2016 | Anastassov ........... A61Q 11/00 424/58 |
| 2016/0250270 A1 * | 9/2016 | Wendschuh ........... A61K 31/01 514/454 |
| 2016/0303010 A1 * | 10/2016 | Prencipe ............... A61Q 11/00 |
| 2018/0042845 A1 * | 2/2018 | Sinai .................... A61K 36/185 |

* cited by examiner

*Primary Examiner* — Isaac Shomer
(74) *Attorney, Agent, or Firm* — Fulwider Patton LLP

(57) ABSTRACT

A toothpaste product that is laced with, or infused with, a sedative such as the active ingredients in cannabis. The act of brushing one's teeth using the present invention transfers the sedative into the bloodstream through contact with the gums, leading to a more restful sleep.

1 Claim, No Drawings

SEDATIVE LACED TOOTHPASTE

CROSS-REFERENCES TO RELATED APPLICATIONS

This is a continuation based U.S. Ser. No. 16/728,256, filed on Dec. 27, 2019, which claims priority from U.S. Ser. No. 62/787,708, filed Jan. 2, 2019, the contents of which are incorporated herein by reference in their entirety.

BACKGROUND

Toothpastes and other oral care products are used to combat tooth decay, gum disease, and overall oral health. Brushing one's teeth before bedtime is a healthy routine recommended for good dental health and shared by many millions of people around the world. It is also known that millions of people suffer from insomnia, restlessness, anxiety, and sleep disorders relating to the inability to relax before a scheduled bedtime. The present invention aims to address the latter problems by utilizing an improved therapeutic toothpaste to be used in the former.

U.S. Pat. No. 9,763,991 entitled Composition For The Treatment Of Neurobehavioral Disorders, the contents of which are fully incorporated herein by reference, teaches the benefits of cannabinol and other derivatives of cannabis to treat insomnia, among other disorders. The '991 Patent extolls the benefit of oral administration of the active ingredient, but lacks a description for the vehicle by which such administration may be safely and routinely carried out. The present invention is directed to a solution to these and other problems.

SUMMARY OF THE INVENTION

The present invention is an oral hygiene product, and particularly a toothpaste product, that is laced into, or infused with, a sedative such as the active therapeutic ingredients in cannabis. The act of brushing one's teeth using the present invention transfers the sedative into the bloodstream through contact with the gums to relax and sedate the user, leading to a more restful sleep. The present invention is healthier than oral administration of narcotics or traditional powerful sleep aids that can be both addicting and hazardous to one's health.

DETAILED DESCRIPTION OF THE PREFERRED EMBODIMENTS

The following descriptions and discussion of the present invention is intended to disclose the inventor's best mode for preparing and practicing the invention. A person of ordinary skill in the art will readily recognize various modifications and substitutions, and the invention is intended to include all such modifications and substitutions. Accordingly, the invention should not be construed as limited to any particular embodiment or example disclosed herein, but rather should include all products and methods covered by the appended claims hereto.

A first embodiment of the present invention is a toothpaste product akin to those used by most people to brush their teeth. In the first preferred embodiment, a toothpaste mixture incorporating the invention is manufactured by producing a pre-wetted binder with a humectant, and then dispersing the mixture into a liquid phase of the formulation. The mixture is blended in a chemical mixer of the type known in the art to form a uniform paste. Alternatively, the binder may be premixed with solid abrasives and then introduced into a mixing liquid phase of the formulation.

Cannabinoids used in this embodiment may be in liquid form, such as that derived as a natural constituent of hemp oil or cannabis oil. In one presenting preferred embodiment, toothpaste is manufactured with one or more cannabinoids incorporated to provide both sedative features and antibacterial effects. In this embodiment, the one or more cannabinoids are naturally derived or artificially derived.

When an oily form of cannabinoids is used, the viscosity of the oil is preferably selected so as to be relatively high, usually in a paste-like matrix. The cannabinoid-containing oil is combined with a binder and a humectant before introduction into the liquid phase. Alternatively, the cannabinoid oil is premixed with the binder and a solid abrasive before introduction into the liquid phase for mixing. Solid and isolated cannabinoids may also be used. Solid cannabinoids may be combined with the binder and a humectant before introduction into the liquid phase. Solid cannabinoids may also be mixed with the binder and a solid abrasive prior to introduction into the liquid phase.

Abrasive agents used in toothpaste manufacturing include hydrated alumina, silica, water-insoluble sodium metaphosphate, tricalcium phosphate, calcium phosphate dihydrate, anhydrous dicalcium phosphate, calcium pyrophosphate, calcium carbonate, sodium bicarbonate, or aluminum silicate. Commercially available abrasive agents such as Zeodent 113, Zeodent 115, or Zeodent 116 (silica abrasive agents) fall within the scope of the present invention, as does a combination of these abrasive agents. A thickener, such as Zeodent 163, may be used together with other cleansing silica materials to thicken the toothpaste to a desirable viscosity.

Binders used in toothpaste manufacturing may be chosen from plant gum such as guar gum or xanthan gum, sodium alginate, karaya gum, bentonite, carrageenan, blanose cellulose gum, methylcellulose, and PEG-1500. Humectants may retain water in the toothpaste matrix and keep toothpaste made according to the instructions from excessively drying out. Sorbitol, glycerin, and propylene glycol may be used as humectants, where Glycerin and sorbitol may also yield a desirable sweet taste to the toothpaste.

In the toothpaste, the one or more cannabinoids may be present at 0.1% to 0.5% by weight, and in some embodiments more specifically at 0.2% to 0.4% by weight. For naturally derived cannabinoids, wherein the hemp oil or cannabis oil has multiple cannabinoids, at least one cannabinoid may be present to comprise between 0.1% and 0.5% by weight of the toothpaste. For artificially derived cannabinoids, adding one isolated purified cannabinoid, preferably chosen from the group comprising of cannabidiol ("CBD"), cannabigerol ("CBG"), tetrahydrocannabinol ("THC"), cannabichromene ("CBC"), and cannabinol ("CBN") is preferred. The amount of the artificial cannabinoid may be at 0.1% to 0.5% by weight of the toothpaste.

Other components of the toothpaste may be used in sufficient amounts, including water, other preservatives, sweeteners, and flavoring oils to prepare and provide a consistent and pleasantly offering paste for use as a commercial toothpaste. Flavoring oils as used this embodiment may be wintergreen, peppermint, spearmint, cinnamon, orange, watermelon, citrus, peach, apricot, anise, vanilla, clove, green tea, caraway, eucalyptus, sage, thyme, bourbon, rye, or other suitable flavors. Multiple flavors in combination may also be added. Coloring agents to give the toothpaste a desirable color may be added. Popular colors are white, blue, red, orange, and green. Coloring agents may be present in the toothpaste at 1% to 3% by weight.

Preservatives suitable for food products and oral application may be added into the toothpaste. Suitable preservatives include citric acid, trisodium citrate, alcohols, benzoates, and dechlorinated phenols. Citric acid and citrates are preferred preservatives for use with the foundation of the invention for use within the formulation of the invention.

Abrasive agents, humectants, binders, and cannabinoids may be combined and mixed in a container, forming the first phase of the method of produces the toothpaste of the invention. The liquid phase, or the second phase, including water, fluoride compounds, preservatives, coloring agents, sweeteners, and flavoring oils, may be combined and mixed. Then, the first phase may be mixed into the second phase and stirred well with a mechanical impeller. Temperature control keeps the mixture from drying out. Components of the tooth powder according to this embodiment are preferably mixed by a solid mixer for even distribution.

The toothpaste according to these embodiments may be safely used by placing a sufficient quantity on a toothbrush. A user then applies agitating force to his or her teeth using the toothbrush with the toothpaste or tooth powder. The user then can rinse his or her mouth with drinking water after brushing as is typical for such use.

Various oral infectious diseases may also be treated with cannabinoid oral care solutions due to their antibacterial, pain relieving, wound dressing, and anti-inflammation properties. Conditions treated by these cannabinoid oral care compositions may include peri-implantitis, periodontitis, oral mucositis (especially oral mucositis caused by chemotherapy in cancer treatment), and dental pain. Cannabinoid dentifrice, including cannabinoid toothpaste, may be used in teeth brushing at a therapeutically effective amount to treat peri-implantitis, periodontitis, oral mucositis, and dental pain.

Example 1

This formulation makes approximately 405 grams of toothpaste.

| Ingredients/Components | Potential Supplier | Percent (%) | Weight (g) |
| --- | --- | --- | --- |
| Sorbo ®, Sorbitol Solution USP/FCC (#260151) | Ingredion/PCC | 27.6448 | 112.00 |
| Emery ™ 917 Glycerine | Emery Oleochemicals/PCC | 26.5587 | 107.60 |
| Water, filtered | municipal | 15.7970 | 64.00 |
| Tixosil 43, amorphous precipitated silica | Solvay/PCC | 8.6390 | 35.00 |
| Tixosil 73, amorphous precipitated silica | Solvay/PCC | 5.1834 | 21.00 |
| Sodium Lauryl Sulfate | Bulk Apothecary | 4.9366 | 20.00 |
| Xylitol | Atlantic Chemical/PCC | 3.0113 | 12.20 |
| SOLEC F, Deoiled Soy Lechithin | SPI Group | 2.2215 | 9.00 |
| Peppermint Oil, Arvensis (SA1120095/5) | Treatt, USA | 1.1107 | 4.50 |
| NATRACOL Titanium Dioxide Dispersible 60% | Roha, USA/PCC | 0.9873 | 4.00 |
| Xanthan Gum, Food Grade, FN | Jungbunzlauer/PCC | 0.8886 | 3.60 |
| Natural Flavor 0.5% NAF A | OGAWA | 0.7405 | 3.00 |
| Sea Salt, Fine | Cargill/PCC | 0.4937 | 2.00 |
| Delta- 9 THC | JOYUS | 0.4937 | 2.00 |
| Benzyl Alcohol | Future Chemical | 0.3949 | 1.60 |
| CBD | JOYUS | 0.2468 | 1.00 |
| Guar Gum | PLT Health/PCC | 0.1975 | 0.80 |
| Stevia-98% REbaudioside A SE | Prescribed For Life | 0.1975 | 0.80 |
| CBN | JOYUS | 0.1234 | 0.50 |
| CBG | JOYUS | 0.1234 | 0.50 |
| Linalool | TRUE TERPENES | 0.0025 | 0.01 |
| Myrcene | TRUE TERPENES | 0.0025 | 0.01 |
| Nerolidol | TRUE TERPENES | 0.0025 | 0.01 |
| Terpinolene | TRUE TERPENES | 0.0025 | 0.01 |
| Totals: | | 100.0000 | 405.14 |

| Finished Product Specification: (Tested outside at Arnesco Laboratories |
| --- |
| Delta-9 THC= |
| Delta-9 CBD= |
| Delta-9 CBN= |
| Delta-9 CBG= |
| Linalool (Terpene)= |
| Myrcene (Terpene)= |
| Nerolidol (Terpene)= |
| Terpinolene (Terpene)= |

Bench Top Procedures:
1) Weigh the silicas and other dry ingredients and premix into quart mason jars.
2) In a Hobart mixer on a scale, add 1 jar of the dry ingredients and weigh the essential oils on top of that mixture.
3) In a 4 oz. mason jar, weigh glycerin and cannabis, mix together, then heat to 180° F. in a water bath for 30 minutes, agitating frequently until homogeneously mixed.
4) Weigh the sodium lauryl sulfate and add to the dry ingredients in the mixer bowl.

5) Weigh the sorbitol and add to the dry ingredients.

6) Weigh the Benzyl Alcohol and add to the dry ingredients.

7) Add the cannabis glycerin mixture to the dry ingredients.

8) Weigh the water, and rinse out container that cannabis was in while agitating and add to dry ingredients, add the terpenes, begin to mix on low speed until dry ingredients hydrate.

9) Finally, mix on high speed for approximately 1 minute to hydrate the gums to stabilize the system so syneresis does not occur through its shelf life.

Examples of changes, substitutions, and alterations are ascertainable by one skilled in the art and could be made without departing from the scope of the information disclosed herein. All references cited are incorporated by reference herein in their entireties and made part of this application.

We claim:

1. A method for manufacturing a cannabis laced toothpaste, comprising:
   1) Introducing silicas into a container;
   2) Forming a mixture by adding an least one essential oil to the silicas;
   3) Modifying the mixture by adding sodium lauryl sulfate;
   4) Adding sorbitol to the mixture;
   5) Adding Benzyl Alcohol to the mixture;
   6) Separately heating a combination of glycerin and cannabis until a homogeneous product is formed;
   7) Adding the glycerin and cannabis product to the mixture to form a composition;
   8) Adding water to the composition;
   9) Adding terpenes to the composition;
   10) Mixing the composition until the composition hydrates.

* * * * *